March 1, 1955 F. MEILLAND Plant Pat. 1,359
ROSE PLANT
Filed May 26, 1954
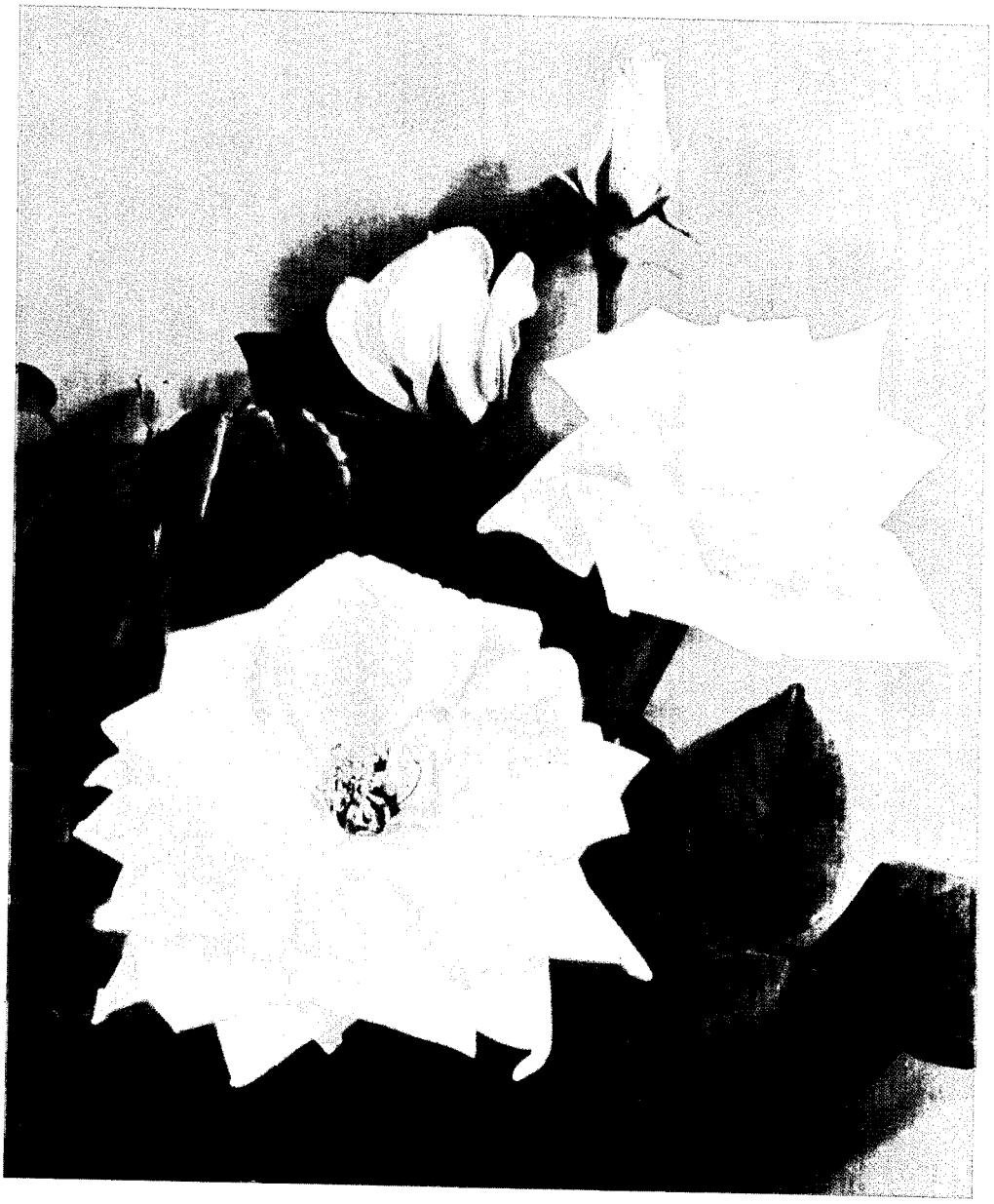
Inventor.
Francis Meilland
By: Robb & Robb
Attorneys.

United States Patent Office

Plant Pat. 1,359

Patented Mar. 1, 1955

1,359

ROSE PLANT

Francis Meilland, Cap Azura, Cap d'Antibes, France, assignor to The Conard-Pyle Company, West Grove, Pa., a corporation of Pennsylvania Application May 26, 1954, Serial No. 432,627

Claims priority, application France July 7, 1953

1 Claim. (Cl. 47—61)

The present invention relates to a new and distinct variety of rose plant of the hybrid tea class, which was originated by me by crossing an unnamed and unpatented seedling derived from a cross of "Virgo" (unpatented) and "Peace" (Plant Patent No. 591), with the unpatented variety "Virgo."

The primary objective in making this cross was to obtain a new variety which combines an upright and bushy habit of growth of the plant, with abundant and healthy foliage, superior floriferousness, good form of the blooms and firm petalage. These desirable characteristics have never heretofore been found in combination in any White variety of rose plant at present known to me in commerce. My objectives were fully achieved, as evidenced by the fact that my new variety is particularly characterized by the excellent, upright, and bushy habits of growth of the plants, their abundant and healthy foliage, superior floriferousness, and excellent form of the White blooms and the firm petalage of the latter.

Asexual reproduction of my new variety by budding in France, as well as at West Grove, Pennsylvania, U. S. A., shows that the foregoing characteristics and distinctions come true to form and are established and transmitted through succeeding propagations.

The accompanying drawing shows typical specimens of the flowers and foliage of my new variety in different stages of development and as depicted in color as nearly true as it is reasonably possible to make the same in a color illustration of this character.

The following is a detailed description of my new variety, with color terminology in accordance with Ridgway's Color Standards and Nomenclature, except where general color terms of ordinary dictionary significance are obvious:

Type: Hardy; bush; outdoor; seedling; for cut flowers and for garden decoration.

Class: Hybrid tea.

Breeding: Seedling.

*Seed parent.*—An unnamed seedling of "Virgo" × "Peace."

*Pollen parent.*—"Virgo."

Propagation: Holds its distinguishing characteristics through succeeding propagations by budding.

FLOWER

Locality where grown and observed: West Grove, Pennsylvania, U. S. A.

Flowers borne: Singly; on stems of medium length and normal strength.

Quantity of bloom: Free, both outdoors and in greenhouse.

Continuity: Continuous.

Fragrance: None.

Bud:

*Peduncle.*—Medium length; medium caliper; erect; almost smooth; with few green prickles. Color—Biscay Green, Plate XVII.

*Before calyx breaks.*—Size—medium. Form—medium length; ovoid; with a conspicuous neck; with very slender foliaceous appendages on the surface of the bud; with slender, entire, bristle-like foliaceous parts extending beyond the tip of the bud equal to ⅛ or more of its length.

*As calyx breaks.*—Color—Clear Dull Green Yellow, Plate XVII.

*As first petal opens.*—Size—medium. Form—medium length; pointed. Color: outside—Pale Viridine Yellow, Plate V, veined with Viridine Yellow, Plate V; inside—Pale Green Yellow, Plate V.

*Opening.*—Opens up well.

Bloom:

*Size (when fully open).*—Medium; from 3¾ inches to 4¼ inches in diameter.

*Petalage.*—Double; from 28 to 35 petals; arranged regularly.

*Form.*—High-centered at first, becoming shallow-cupped; petals being at first loosely rolled outward, and remaining loosely rolled outward to maturity.

Petals: Medium thickness; leathery; inside satiny; outside shiny.

*Shape.*—Outer petals—obovate; usually no notches. Intermediate petals—obovate; usually no notches. Inner petals—obovate; irregular; with 1 or 2 notches.

This description of a newly opened flower was made from a rose grown in a greenhouse in the month of April, at West Grove, Pennsylvania, U. S. A.:

*Color.*—Outer petal: Outside surface—white, veined with Pale Yellow Green, Plate VI towards base of petal; point of attachment Viridine Green, Plate VI. Inside surface—white, veined with Viridine Green, Plate VI towards base; point of attachment Light Green Yellow, Pale V bordering a main vein of Viridine Yellow, Plate V. Intermediate petal: Outside surface—white, shading into Sulphur Yellow, Plate V, veined with Green Yellow, Plate V. Inside surface—white, shading into Pale Green Yellow, Plate V towards base, veined with Viridine Yellow, Plate V; point of attachment Light Viridine Yellow, Plate V. Inner petal: Outside surface—white, veined towards base with Viridine Yellow, Plate V. Inside surface—white, veined towards base with Viridine Yellow, Plate V; basal area Pale Viridine Yellow, Plate V.

This description was made from a rose that was open for three days in a greenhouse in the month of April, at West Grove, Pennsylvania, U. S. A.:

*Color.*—Outer petal: Outside surface—white, with vein of Light Lumiere Green, Plate XVII extending from base part of the way up the petal. Inside surface—white, lightly veined towards base with Light Viridine Yellow, Plate V; point of attachment Pale Green Yellow, Plate V. Inner petal: Outside surface—white, with thin veins of Light Viridine Yellow, Plate V; point of attachment Greenish Yellow, Plate V. Inside surface—white, shading to Pale Green, Yellow, Plate V at base; lower half of petal lightly veined with Light Viridine Yellow, Plate V.

*General color effect.*—Newly opened flower—white. 3-days open—white.

*Flower longevity.*—Cut roses grown in greenhouse and kept at living-room temperatures—4 days in the month of April.

REPRODUCTIVE ORGANS

Stamens: Medium number; arranged irregularly about pistils; mixed with petaloids; tucked in calyx.

Filaments: Many; most with anthers; long. Color—Eosine Pink, Plate I.

Anthers: Open at various times; medium size; occasionally an anther fused with a petaloid. Color—Baryta Yellow, Plate IV.

Pollen: Moderate to abundant. Color—gold.

Pistils: Medium number.

Styles: Uneven; medium length; medium caliper; bunched.

Stigma: Color—pale yellow.

Ovaries: Some protruding from calyx.

Hips: None.

Sepals: Permanent; moderately long; straight.
Seeds: None.

PLANT

Foliage:

*Leaves.*—Usually compound of 5, but occasionally 7, leaflets; normal abundance; medium size; moderately thin; leathery.

*Leaflets.*—Shape—ovoid, with apex cuspidate. Base—round. Margin—simply serrate.

*Color.*—Mature: upper surface—Varley's Green, Plate XVIII; under surface—Chromium Green, Plate XXXII. Young: upper surface—Biscay Green, Plate XVII; under surface—Dark Vinaceous, Plate XXVII, overlying Scheele's Green, Plate VI.

*Rachis (the supporting stem of the compound leaf).*—Medium caliper. Upper side—grooved; hairy in groove; prickly on edge. Under side—moderately thorny.

*Stipules.*—Medium length; moderately narrow; with medium length points turning out at an angle of more than 45°.

*Disease resistance.*—Good resistance to blackspot, mildew and rust as compared with other varieties grown under comparable cultural conditions at West Grove, Pennsylvania, U. S. A., and in France.

*Frost resistance.*—Excellent as compared with other varieties grown under comparable cultural conditions at West Grove, Pennsylvania, U. S. A., and in France.

Growth:

*Habit.*—Bushy; upright; much-branched.

*Growth.*—Free.

*Canes.*—Medium caliper.

*Main stems.*—Color—Cerro Green, Plate V. Thorns—many; medium length; pointed downward; with short, oval base. Prickles—none. Hairs—none.

*Branches.*—Color—Grass Green, Plate VI. Thorns—several; medium length; usually straight, but some pointed downward; with short, oval base. Prickles—none. Hairs—none.

*New shoots.*—Color—Parrot Green, Plate VI. Thorns—several; medium length; straight; with short, oval base. Prickles—several. Color—green-brown. Hairs—none.

I claim:

A new and distinct variety of rose plant of the hybrid tea class, substantially as herein shown and described, characterized particularly as to novelty by the combination of the upright and bushy habit of growth of the plant, the abundant and healthy foliage of the plant and its superior floriferousness, the superior form of its White blooms, and the firm petalage thereof.

No references cited.